(12) United States Patent
Momot et al.

(10) Patent No.: US 6,672,868 B1
(45) Date of Patent: *Jan. 6, 2004

(54) METHOD OF TRANSILLUMINATION IMAGING OF TEETH

(75) Inventors: Tomasz Momot, Ossining, NY (US); Adam Jacobs, Woodcliff Lake, NJ (US)

(73) Assignee: Electro-Optical Sciences Inc., Irvington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/991,897

(22) Filed: Nov. 23, 2001

(51) Int. Cl.⁷ .................................................. A61C 1/00
(52) U.S. Cl. ........................................ 433/29; 382/100
(58) Field of Search ................... 433/29, 215; 382/100, 382/115, 128

(56) References Cited

U.S. PATENT DOCUMENTS

| | | | | | |
|---|---|---|---|---|---|
| 4,184,175 | A | * | 1/1980 | Mullane, Jr. | 358/93 |
| 5,440,393 | A | * | 8/1995 | Wenz | 433/29 |
| 5,476,095 | A | * | 12/1995 | Schnall et al. | 128/653.2 |
| 5,718,666 | A | * | 2/1998 | Alarcon | 600/249 |
| 5,865,621 | A | * | 2/1999 | Calderwood | 433/116 |
| 6,201,880 | B1 | * | 3/2001 | Elbaum et al. | 382/100 |

* cited by examiner

Primary Examiner—John J. Wilson
(74) Attorney, Agent, or Firm—Rodney T. Hodgson

(57) ABSTRACT

An means for blocking light reflected from the surface of a tooth from the imaging system while imaging light transilluminated through the tooth is presented.

16 Claims, 4 Drawing Sheets

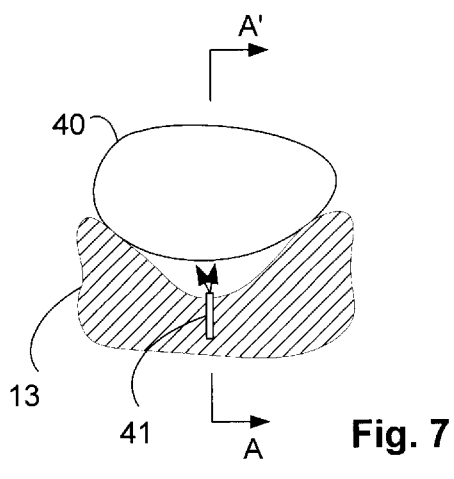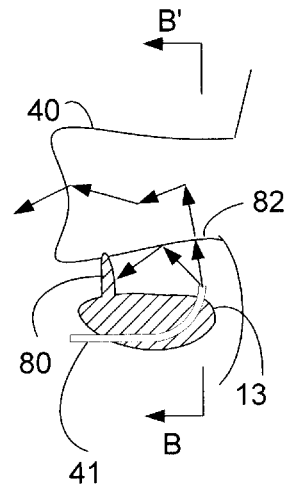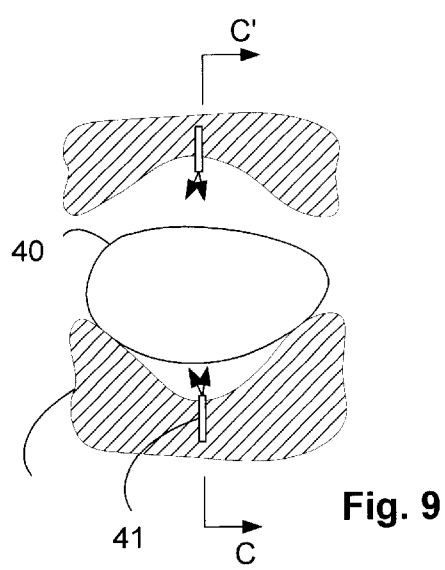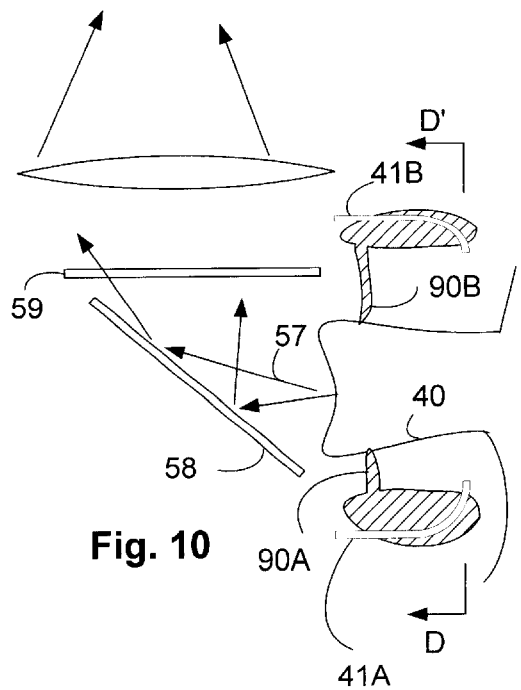

METHOD OF TRANSILLUMINATION IMAGING OF TEETH

RELATED APPLICATIONS

This application is related to U.S. application Ser. No. 09/722,248, filed Nov. 24, 2000 (now U.S. Pat. No. 6,341,957), and to U.S. application Ser. No. 09/670,492, filed Aug. 26, 2000 by the present inventors, and to U.S. application Ser. No. 08/778,001 filed Dec. 31, 1996, (now U.S. Pat. No. 6,201,880, issued on Mar. 13, 2001). The present application is related to U.S. application Ser. No. 09/407,344, now abandoned, and Ser. No. 09/407,345 filed on Dec. 20, 1999 now U.S. Pat. No. 6,294,443 and U.S. Provisional Application No. 60/167,711 filed Nov. 27, 1999 by the same inventors as the present invention. The above identified applications which are assigned to the assignee of the present invention are incorporated herein by reference in their entirety including incorporated material.

FIELD OF THE INVENTION

The field of the invention is the field of imaging of teeth in a mouth.

BACKGROUND OF THE INVENTION

The above identified US patents and patent applications summarize the background of the art in great detail. In brief, the prior art to the above identified applications is deficient in that images of teeth taken with light transillumination were not reproducible. The above identified applications teach that the illumination source and imaging system may be held in a reproducible and repeatable position with respect to the tooth by anchoring the source and imaging system physically with respect to the tooth. Prior art sources of light for transillumination tend to produce extraneous light scattered into an imaging system if a broad area light is used as a light source, and tend to produce non-uniform illumination if a small area light source is used.

SUMMARY OF THE INVENTION

The present invention is a method, apparatus, and system for digital imaging of teeth through transillumination of teeth in a mouth. The invention comprises using an elastomeric locator which contacts both a proximal surface of a tooth and the gum holding the tooth. The elastomeric locator is physically connected both to a light source for illuminating the tooth and to imaging optics which conduct light from the light source which has been transmitted through the tooth to an image receiver such as a CCD array, a vidicon, a CMOS imaging array, photographic film, or other image receiving devices which may form an image of the tooth. A means for blocking light reflected from the side of the tooth from reaching the imaging optics is included. Elastomeric location stubs fit between two teeth to more precisely locate the illumination and imaging system.

BRIEF DESCRIPTION OF THE DRAWINGS

FIG. 7 is a plan view of an illumination system.

FIG. 8 is a drawing of a preferred embodiment of the invention.

FIG. 9 is a plan view of an illumination system.

FIG. 10 is a drawing of the most preferred embodiment of the invention.

DETAILED DESCRIPTION OF THE INVENTION

The present inventors have found that transillumination imaging of teeth is difficult when the side of the tooth is illuminated, and the top (occlusal) surface of the tooth must be imaged. Since the light used for imaging is injected in one surface, and then scatters greatly in the tooth, the transilluminating light exiting at another surface is much less bright than the light reflected from the tooth and backscattered from the injected surface. (Backscattered light may be defined as scattered light which has not progressed very far in the tooth and which exits near the entry point). The inventors have found that the reflected light (here defined as the reflected and backscattered light combined) enters the optical system and washes out the image of the occlusal surface, as well as causes unwanted artifacts in the image. The inventors experimented with blocking means to block the unwanted light, and found that black electricians tape around the tooth worked well. However, such a means is difficult to apply in vivo, and other and more preferred embodiments discovered.

Figure 1:
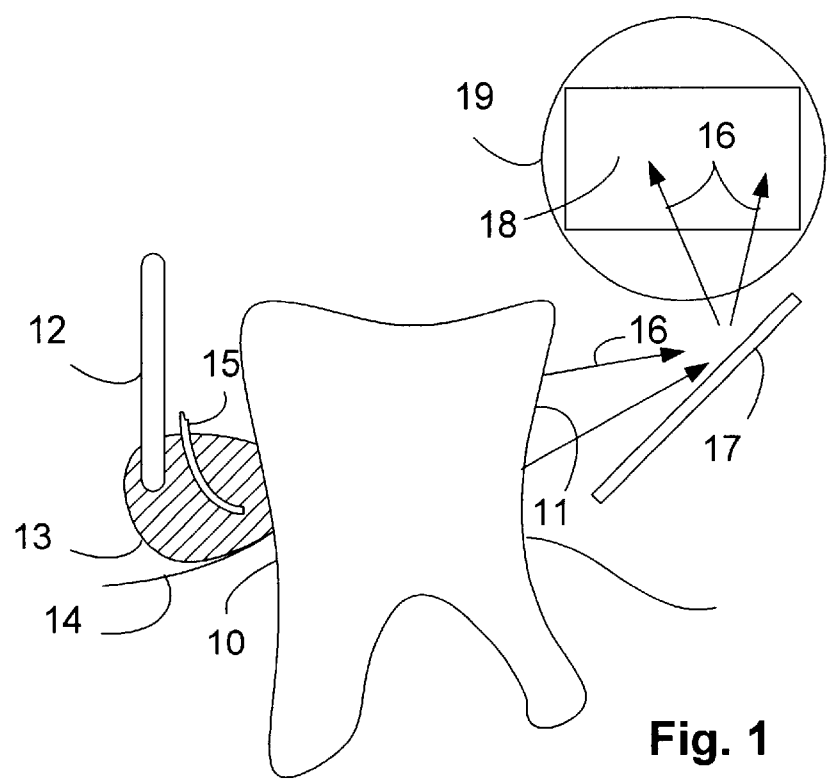
FIG. 1 shows a sketch of light transilluminating a tooth.

FIG. 1 shows sketch where a labial or lingual surface 11 of the tooth 10 is imaged. A body 12 is held in a reproducible position with respect to tooth 10 by means of an elastomeric locator 13. The locator 13 may be shaped with a V shaped groove (shown later) which fits between tooth 10 and neighboring teeth. The elastomeric locator may also rest against the gum 14 holding the tooth 10. A source of light such as a light pipe 15 shines light on a labial or buccal surface of the tooth 10. The light enters the tooth and is scattered within the tooth. Some of the light 16 which is scattered in the tooth 10 exits the surface 11 of the tooth 10. We call such a process transillumination of the tooth. Light 16 exits the surface 11 and is directed to mirrors 17 and 18 held in a known position (connection not shown) with respect to body 12 by a holding means 19. Surface 11 is imaged in an imaging system (not shown) using light 16

Figure 2:
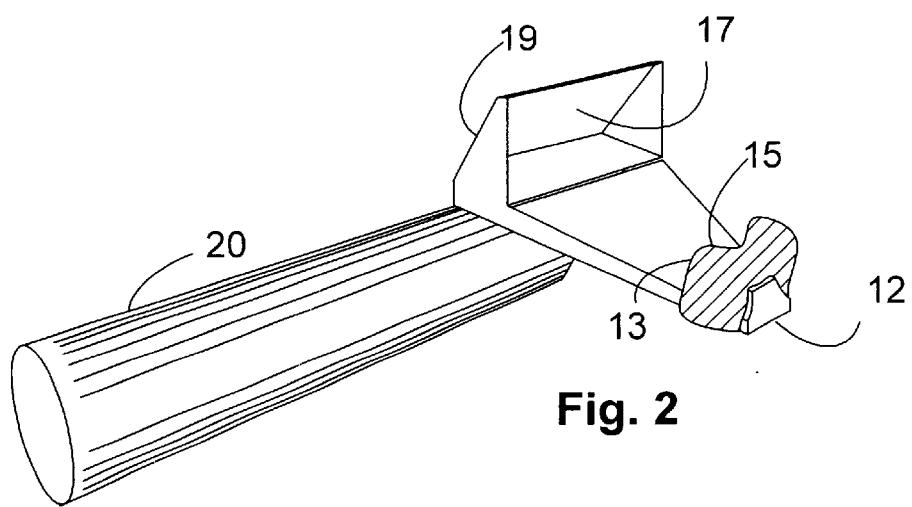
FIG. 2 shows a perspective sketch of a mouthpiece for transillumination imaging.

FIG. 2 shows an adaptation of a perspective sketch of a disposable mouthpiece described in U.S. application Ser. Nos. 09/722,248, 09/407,344 and 09/407,345. A handle 20 for conducting light from a tooth and imaging a labial or buccal surface of the tooth while illuminating the opposite side of the tooth is shown. Light from a handpiece (not shown) is brought into the handle 20, and an optical light pipe, whose position is shown as 15 in FIG. 2, brings the light around to a position at the base of the elastomeric locator 13 from whence the surface of the tooth is illuminated. The entire body 12 holding locator 13, light pipe 15, and mirror 17 rotates around an axis perpendicular to the handle 20 so that the buccal and labial surfaces of the tooth 10 may be illuminated and imaged in turn.

Figure 3:
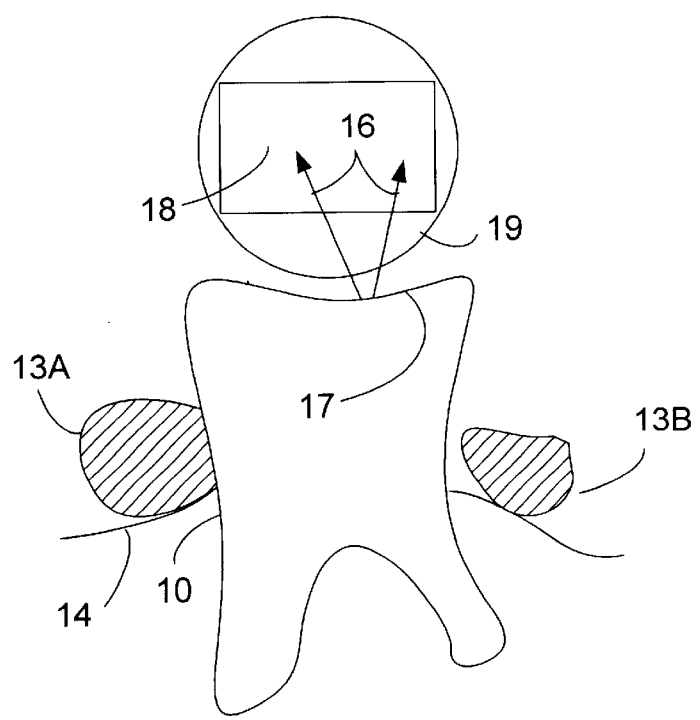
FIG. 3 shows an elevation sketch of illuminating a tooth through a non-occlusal surface and imaging the occlusal surface using the transilluminated light.

FIG. 3 shows an elevation view of a tooth, where the occlusal surface 17 of tooth 10 is imaged using light incident from either the labial or buccal surface or from both surfaces simultaneously. In FIG. 3, two elastomeric locators 13A and 13B are shown. Light pipes (not shown) may be included in one or both of the elastomeric parts 13A and 13B. A part of an imaging system is shown schematically.

Figure 4:
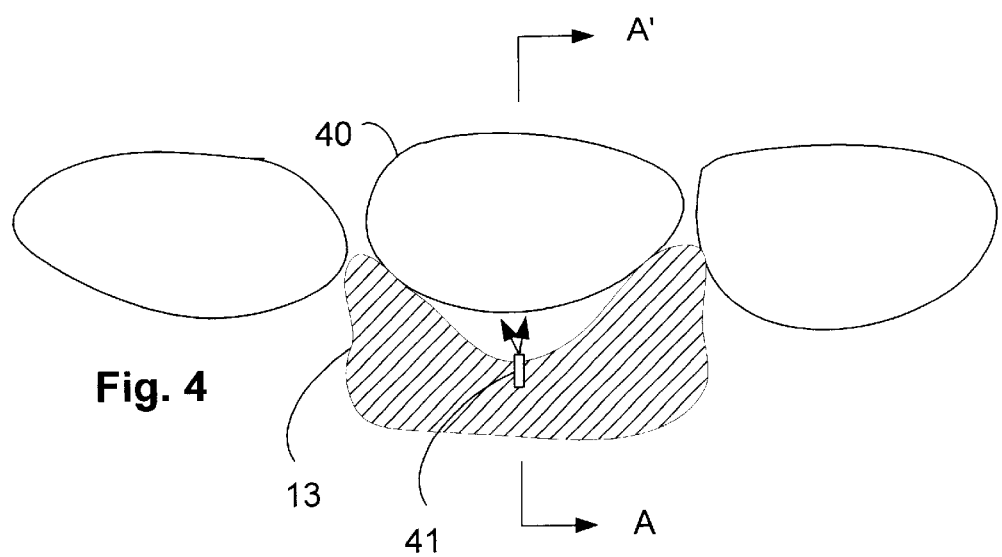
FIG. 4 is a plan view of a number of teeth "in vivo" showing the position of the illumination system.

FIG. 4 shows a plan view of a preferred embodiment of the invention showing a "v" shaped elastomeric locator with the tips of the "v" contacting the proximal surfaces of tooth 40, where the light source 41 is held away from the tooth and in position to illuminate the tooth, while the occlusal surface of the tooth is imaged.

Figure 5:
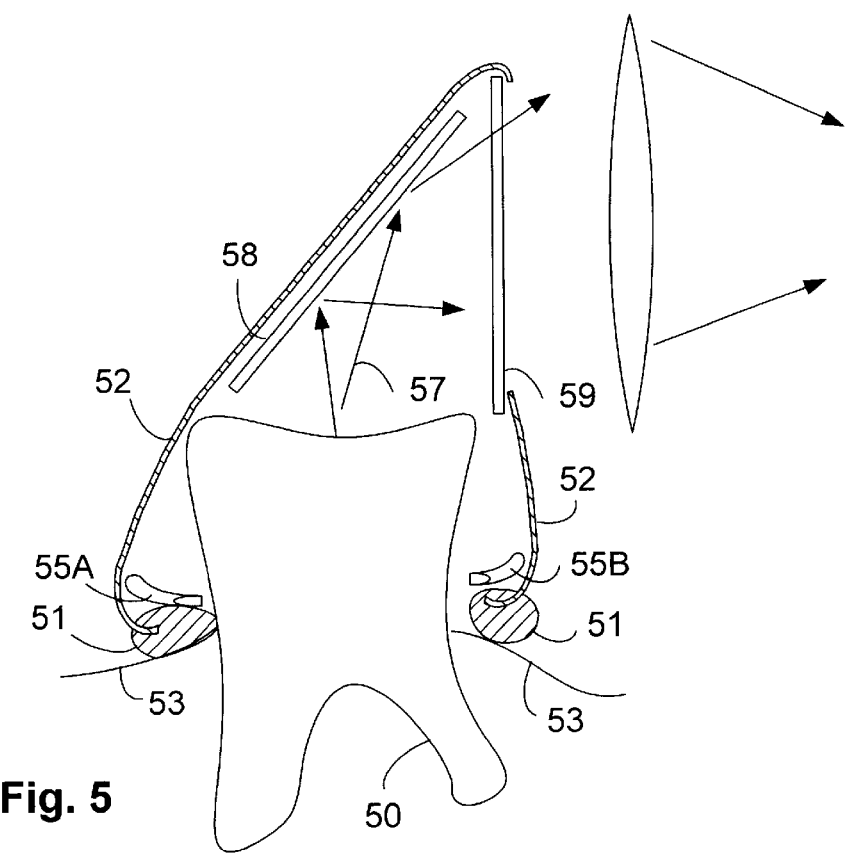
FIG. 5 is a drawing of two surfaces of a tooth illuminated while the occlusal surface is imaged.

FIG. 5 shows a sketch of an elevation view of the optical system for viewing the occlusal surface of a tooth 50. A holder 52 slips down over the tooth 50 and elastomeric pads 51 rest on the gum 53 and/or the proximal surfaces of the tooth 50 to hold the holder 52 in place. Optical fibers 55A and 55B bring light from a handle (not shown) to illuminate both buccal and labial surfaces of the tooth 50. Light 57 which has been scattered in the tooth exits the occlusal surface of the tooth, strikes mirror 58, and is directed through a transparent window 59 to an imaging system (shown later).

Figure 6:
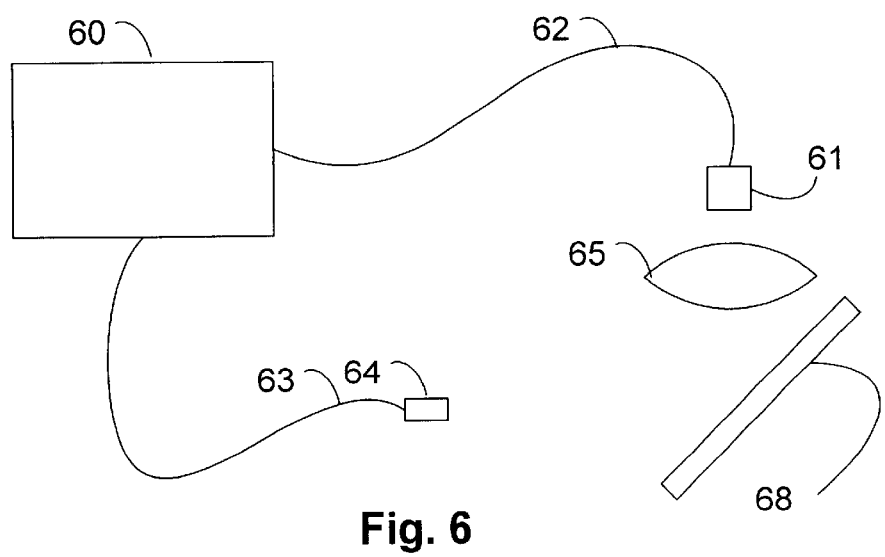
FIG. 6 is a block drawing of the system of the invention.

FIG. 6 shows a block diagram of the transillumination imaging system of the invention. Light reflected from mirror 18 or 58 may be further reflected in other mirrors 68 and finally passed through a lens 65 so that the surface of the tooth 50 is imaged on an image receiver 61. The image receiver 61 may be photographic film, a vidicon, a CCD array, or a CMOS detector, all of which are well known to those of ordinary skill in the art of imaging, or any other image detector as is known or will become known in the art of image receiving and processing. The electronic signals from an electronic image receiver may be passed over line 62 to a controller 60 which controls light from a lighting device 64 which provides light for illuminating the tooth. The signals to control the light are passed over line 63. The controller is or is connected to a computer which may display the image on an imaging device such as a computer monitor screen and/or print out images on a printer device. All of such devices as are known in the art may be included in the controller 60 or may be stand-alone devices or may be any combination of stand alone devices and integrated devices. Line 62 may be instead a wireless link. The controller 60 may further pass images or modified images to remote controllers and/or data storage and display facilities.

FIGS. 7 and 8 show plan and elevation views of a preferred embodiment of the invention. FIG. 7 shows a cut along B–B' of FIG. 8. FIG. 8 shows an elevation view through the cut A–A' of FIG. 7, showing an embodiment of the invention as a flap 80 which blocks light 81 from the light pipe 41 which reflects off the surface 82 of the tooth 40. The flap 80 may be conveniently molded of the same elastomeric material in the same molding step as locator 13 so that flap 80 and locator 13 are one monolithic block.

FIGS. 9 and 10 show plan and elevation views of the most preferred embodiment of the invention. FIG. 10 shows an elevation view through the cut C–C' of FIG. 9, showing an embodiment of the invention as a flaps 90A and 90B which block light from the light pipes 41A and 41B which reflects off the labial and buccal surfaces of the tooth 40.

The light which has transilluminated the tooth and exits the occlusal surface of the tooth is much less bright than the light which has reflected from the surface of the tooth, since the transilluminated light is scattered greatly by the material of the tooth and attenuated in part in the tooth. The directly reflected light may not be imaged, but it contributes to lack of contrast and may in fact completely wash out the image of the occlusal surface.

Other means of blocking the reflected light may be used in place of the preferred elastomeric flap of the invention, but in the preferred embodiments the means for blocking the light should touch the tooth, and most preferably should form an uninterrupted light seal around the entire tooth.

Obviously, many modifications and variations of the present invention are possible in light of the above teachings. It is therefore to be understood that, within the scope of the appended claims, the invention may be practiced otherwise than as specifically described.

We claim:

1. A method of transillumination imaging of a tooth in vivo in a mouth, comprising:
    a) placing an elastomeric locator in a position against a surface in the mouth; then
    b) illuminating a non-occlusal surface of the tooth using at least one illumination means held in a known position with respect to the elastomeric locator; and then
    c) imaging the occlusal surface of the tooth using light from the illumination means which has tansilluminated the tooth, wherein the imaging is performed with an imaging system held in a known position with respect to the elastomeric locator, wherein at least one blocking means is used for blocking light from the illumination means which is reflected from the illuminated non-occlusal surface of the tooth, the reflected light blocked from entering the imaging system.

2. The method of claim 1, where the elastomeric locator has a "v" shaped surface for contacting a proximal surface of the tooth and holding the illumination means away from the tooth.

3. The method of claim 2, where the illumination means is a fiber optic illumination means.

4. The method of claim 1, where a first illumination means illuminates the buccal surface of the tooth, and a second illumination means illuminates the labial surface of the tooth.

5. The method of claim 4, where the means for blocking light are two elastomeric flaps held fixedly in position with respect to the elastomeric locator, the elastomeric flaps for contacting the buccal and labial surfaces of the tooth.

6. The method of claim 5, where the elastomeric flaps and the elastomeric locator are formed together in the same molding operation.

7. The method of claim 1, where the means for blocking light is an elastomeric flap held fixedly in position with respect to the elastomeric locator, the elastomeric flap for contacting the non-occlusal surface of the tooth.

8. The method of claim 7, where the elastomeric flap and the elastomeric locator are formed together in the same molding operation.

9. The method of claim 1, where the elastomeric locator contacts a gum near the tooth.

10. The method of claim 9, where the elastomeric locator has a "v" shaped surface which contacts a proximal surface of the tooth and holds the illumination means away from the tooth.

11. An apparatus for transilluminating and imaging a tooth in vivo in a mouth, comprising;
    a) an elastomeric locator for placing against a surface in the mouth;
    b) at least one illumination means for illuminating a non-occlusal surface of the tooth, the illumination means held in a known position with respect to the elastomeric locator;
    c) an optical system for conveying light from the illumination means which has transilluminated the tooth to an image receiver, wherein the image receiver is held in a known position with respect to the elastomeric locator; and d) at least one blocking means for blocking light from the illumination means which is reflected from the illuminated non-occlusal surface of the tooth, the reflected light blocked from entering the optical system for conveying light.

12. A system for transilluminating and imaging a tooth in vivo in a mouth, comprising;

a) an elastomeric locator for placing against a surface in the mouth;

b) at least one illumination means for illuminating a non-occlusal surface of the tooth, the light source held in a known position with respect to the elastomeric locator;

c) an image receiver held in a known position with respect to the elastomeric locator;

d) an optical system, for conveying light from the illumination means which has transilluminated the tooth to the image receiver, the transilluminated light exiting the occlusal surface of the tooth;

e) at least one blocking means for blocking light from the illumination means which is reflected from the illuminated non-occlusal surface of the tooth, the reflected light blocked from entering the optical system; and f) a controller for controlling the illumination means.

13. The system of claim 12, further comprising a display apparatus for displaying an image received by the image receiver.

14. The system of claim 12, further comprising storage means for storing the image received by the image receiver.

15. The system of claim 12, further comprising image transmission means for transmitting the image received by the image receiver.

16. The system of claim 12, further comprising computer means for modifying the image received by the image receiver.

* * * * *